United States Patent [19]

Finke et al.

[11] 4,013,715
[45] Mar. 22, 1977

[54] PROCESS FOR THE MANUFACTURE OF 2-HALO-ETHANE-PHOSPHONIC ACID DIHALIDES AND VINYL-PHOSPHONIC ACID DIHALIDES

[75] Inventors: Manfred Finke, Fischbach, Taunus; Hans-Jerg Kleiner, Bad Soden, Taunus, both of Germany

[73] Assignee: Hoechst Aktiengesellschaft, Frankfurt am Main, Germany

[22] Filed: Nov. 18, 1974

[21] Appl. No.: 524,812

[30] Foreign Application Priority Data

Nov. 19, 1973 Germany .......................... 2357676

[52] U.S. Cl. ..................... 260/543 P; 260/502.4 R
[51] Int. Cl.² ............................................ C07F 9/38
[58] Field of Search ............................... 260/543 P

[56] References Cited

UNITED STATES PATENTS

| | | | |
|---|---|---|---|
| 3,200,145 | 8/1965 | Lutz et al. | 260/543 P |
| 3,574,735 | 4/1971 | Sennewald et al. | 260/543 P |
| 3,776,953 | 12/1973 | Maier | 260/543 P |
| 3,943,170 | 3/1976 | Kleiner | 260/543 P |
| 3,962,324 | 6/1976 | Kleiner | 260/543 P |

FOREIGN PATENTS OR APPLICATIONS 2,132,962  9/1963  Germany

*Primary Examiner*—Ethel G. Love
*Attorney, Agent, or Firm*—Curtis, Morris & Safford

[57] ABSTRACT

2-Halo-ethane-phosphonic acid dihalides and vinyl-phosphonic acid dihalides are prepared by reacting hydroxyethane-phosphonic acid, its salts or functional derivatives, or the mono-thio-analogs thereof with acid halides of the formula $(CO)_{1 \text{ or } 2}X_2$ wherein X represents halogen using as catalyst a compound containing at least one three- to penta-valent nitrogen or phosphorus atom bound by at least 3 valences to organic radical having up to 20 carbon atoms, two of the valences possibly forming a double bond; a one- to three-basic organic or inorganic fully amidated acid of three or penta-valent phosphorus the nitrogen atoms of which are alkylated by aliphatic radicals having up to 20 carbon atoms and the organic radical of which contains up to 20 carbon atoms, or a mixture of the aforesaid compounds. If desired the reaction is carried out in an inert solvent, preferably the reaction product and in the presence of a polymerization inhibitor.

24 Claims, No Drawings

PROCESS FOR THE MANUFACTURE OF 2-HALO-ETHANE-PHOSPHONIC ACID DIHALIDES AND VINYL-PHOSPHONIC ACID DIHALIDES

This invention relates to a process for the manufacture of 2-halo-ethane-phosphonic acid dihalides and vinyl-phosphonic acid dihalides.

It is known from German Pat. No. 1,123,667 to prepare 2-chloro-ethane-phosphonic acid dichloride by reacting phosphorus trichloride and ethylene with oxygen under pressure. Owing to the high pressure special apparatus is required and the low conversion rate to the desired product necessitates the use of a large surplus of ethylene and phosphorus trichloride. As by-products there are formed a considerable amount of phosphorus oxichloride, which can only be used in other synthesis after a complicated purification, and chloro-ethoxy-phosphoryl chloride, which cannot be separated by distillation from the 2-chloro-ethane-phosphonic acid dichloride.

According to Kabachnik and collaborators (Chem. Abstr. 42, (1948), pages 7241 – 43) tris-2-chloroethyl phosphite is obtained in a good yield besides a non distillable polycondensate when 1 mole of phosphorus trichloride is reacted with 3 moles of ethylene oxide. The tris-2-chloro-ethyl phosphite thus obtained can be subjected to a rearrangement to yield the bis-2-chloro-ethyl ester of 2-chloro-ethane-phosphonic acid. In this reaction a non distillable polycondensate is also formed. According to German Offenlegungsschrift No. 2,132,962 the reaction mixture can be reacted with phosgene at a temperature above 90° C in the presence of suitable catalysts whereby 2-chloro-ethane-phosphonic acid dichloride is obtained in a good yield besides a small amount of vinyl-phosphonic acid dichloride. It is also possible, of course, to use for this reaction the pure bis-2-chloroethyl ester of 2-chloro-ethane-phosphonic acid.

German Offenlegungsschrift No. 2,023,050 proposes the chlorination of ethane-phosphonic acid dichloride with elemental chlorine to 2-chloro-ethane-phosphonic acid dichloride. It is a drawback of this reaction that small amounts of 1-chloro-ethane-phosphonic acid dichloride are formed the distillative separation of which is rather difficult.

The present invention provides a process for the manufacture of 2-halo-ethane-phosphonic acid dihalides and vinylphosphonic acid dihalides of the formulae I and II

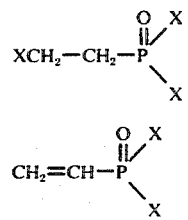

in which X represents halogen, preferably chlorine or bromine, which comprises reacting, optionally in the presence of an inert solvent and a polymerization inhibitor, 2-hydroxyethane-phosphonic acid of the formula III

its salts or functional derivatives or the mono-thio-analogs of the said compounds with acid halides of the formula IV

in which X has the meaning given above and n stands for 1 or 2, in the presence of a catalyst consisting of a. a compound containing at least one three to pentavalent nitrogen or phosphorus atom bound by at least three valences to organic radicals having up to 20 carbon atoms, two of the valences possibly forming a double bond, or b. a one to three-basic organic or inorganic fully amidated acid of three or pentavalent phosphorus the nitrogen atoms of which are alkylated by aliphatic radicals having up to 20 carbon atoms and the organic radical of which contains up to 20 carbon atoms, or c. a mixture of the aforesaid compounds.

Suitable salts of 2-hydroxyethane-phosphonic acid are preferably the alkali metal and ammonium salts and suitable functional derivatives are, for example, the diesters, monoesters or the salts thereof, pyrophosphonic acid esters, as well as the thio-analogs of the said compounds, i.e. the corresponding derivatives of 2-hydroxyethane-thiophosphonic acid. The free acids, the salts and neutral esters thereof are preferred as starting compounds because they are easily accessible. The chemical nature of the ester group is not critical, however, for practical reasons the low molecular weight alkyl esters having from 1 to 6 carbon atoms are preferred.

The following compounds can be used as starting material, for example, 2-hydroxyethane-phosphonic acid dimethyl ester, diethyl ester, dipropyl ester, di-n-butyl ester, diisobutyl ester, dioctyl ester, didodecyl ester, the corresponding semi-esters and their sodium salts, 2-hydroxyethane-phosphonic acid, the mono- or disodium salt of 2-hydroxyethane-phosphonic acid.

The starting compounds can be prepared, for example by hydrolysis of 2-acetoxyethane-phosphonic acid diesters, which can be obtained in simple manner on an industrial scale by the process disclosed in German Offenlegungsschrift No. 2,127,821. Complete hydrolysis yields 2-hydroxyethane-phosphonic acid while partial hydrolysis gives 2-hydroxyethane-phosphonic acid diesters as already ascertained.

It has also been proposed to prepare 2-hydroxyethane-phosphonic acid derivatives by the addition of ethylene oxide on sodium salts of phosphorous acid (of. J.Prat et al. Mem. Services chim. etat, 34, page 393 (1948); C.A. 44, 5880i (1950)). The process of the present invention allows of using as starting material contaminated phosphorous acid obtained as waste product in several industrial processes. It is, without doubt, an industrial progress when phosphorous acid of the aforesaid type can be used to prepare the reaction products in accordance with the present invention.

Suitable inert solvents are, for example, trichloroethane, tetrachloroethane, trichloroethylene, perchloroethylene, toluene, chlorobenzene, dichlorobenzene, diphenylmethane, chloronaphthalene, or the final product of the reaction according to the invention which is preferred.

As acid halides of formula IV there are preferred those in which X represents chlorine or bromine, i.e. phosgene, oxalyl chloride, bromophosgene and oxalyl bromide, phosgene being preferred.

The reaction is carried out under the conditions specified in German Offenlegungsschrift No. 2,129,584. As catalysts compounds are used which contain at least one tertiary or quaternary nitrogen or phosphorus atom, i.e. which is bound by three or four valences to carbon, two valences possibly forming a double bond.

Compounds of this type have the formulae V, VI, or VII

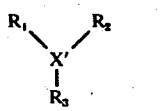

$R_1-CH=X'-R_2$     (VI),

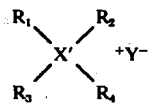

in which X' represents a nitrogen or phosphorous atom, Y represents an inorganic or organic acid radical, for example a halogen ion the $SO_4^{--}$ ion or the ion of an organic sulfonic acid, for example $CH_3OSO_3^-$ or $C_6H_5SO_3^-$, and $R_1$, $R_2$, $R_3$, and $R_4$ represent identical or different organic radicals, such as straight chain or branched alkyl radicals having from 1 to 20, preferably from 1 to 12 and more preferably from 1 to 4 carbon atoms, alkenyl radicals having from 2 to 20, preferably from 2 to 12 and more preferably from 2 to 4 carbon atoms, cycloalkyl radicals having from 4 to 8, preferably from 4 to 6 carbon atoms, or phenyl or benzyl groups or acyl groups having from 1 to 4 carbon atoms, preferably 1 to 2 carbon atoms; all radicals $R_1$ to $R_4$ possibly being substituted, preferably once, by halogen, preferably chlorine and/or bromine, or alkoxy having from 1 to 4 and preferably 1 to 2 carbon atoms, or a dialkyl-amino group the alkyl groups of which have from 1 to 4 carbon atoms. Two of the radicals $R_1$ to $R_4$ may form a ring, as for example in N-methyl-pyrrolidone, pyridine, or 1-methylphospholene. The catalyst used preferably has a molecular weight of up to 500, preferably up to 200.

Further suitable catalysts are nitrogen- or phosphorus containing compounds in which the nitrogen or phosphorus is bound by three valences to carbon and which have the formula VIII

in which Z represents oxygen and, if X is phosphorus, Z also represents sulfur, two halogen atoms, preferably two chlorine atoms, or the group $NR_5$ in which $R_5$ has the same meaning as $R_1$ or represents hydrogen. In this case, too, 2 or 3 of the radicals $R_1$ to $R_3$ may form a cycle, optionally with inclusion of a hetero-atom, for example oxygen, sulfur, or nitrogen.

Amides of the various organic or inorganic one to three basic acids of three or pentavalent phosphorus can also be used as catalysts. Catalysts of this type are peramidated, they carry at the nitrogen atom(s) 2 aliphatic radicals each, having up to 20 carbon atoms, preferably alkyl radicals having from 1 to 4 carbon atoms, and as organic radical at the phosphorus atom an aliphatic radical having up to 20 carbon atoms, preferably an alkyl radical having from 1 to 4 carbon atoms or a cyclo-alkyl radical having from 4 to 8 carbon atoms, or a phenyl or benzyl group, the said aliphatic radical possibly being substituted, preferably by low molecular weight alkyl or alkoxy radicals or halogen atoms.

The following catalysts can be used: p-chloro-benzalaniline

A. Tertiary aliphatic and aromatic amines and phosphines such as trimethylamine, triethylamine, tripropylamine, tributylamine, triphenylamine, trimethyl phosphine, triethyl phosphine, tripropyl phosphine, tributyl phosphine, triphenyl phosphine, and tris(p-dimethylaminophenyl)-phosphine, and the corresponding mixed amines, phosphines, phospholanes, and phospholenes, such as dimethylethylamine, diethylbutylamine, N-dimethylaniline, 4-methyl-N-dimethylaniline, diethylaniline, N,N-tetramethylphenylene diamine, or N-methylpyrrolidone; methyldiethyl phosphine, dimethylpropyl phosphine, diethylbenzyl phosphine, 1-methylphospholene-3 and 1-ethyl-3-methylphospholene-3.

B. Azomethines such as hydrobenzamide, benzalaniline, o-, m-, p-methyl-, o-, m-, p-methoxy-, o-, m-, p-chloro-benzalaniline as well as corresponding derivatives of substituted anilines, for example of o-, m-, p-toluidine, of o-, m-, p-nitraniline, of o- and p-anisidine and of o-, m-, and p-chloroniline.

C. Quaternary ammonium salts or phosphonium salts such as tetramethylammonium chloride or bromide, tetraethyl-phosphonium chloride, trimethylbenzylammonium chloride, triethylbenzylammonium chloride, trimethylbenzyl-phosphonium chloride, triphenylethyl-phosphonium-2,4-diaminobenzene sulfonate.

D. Heterocyclic compound having aromatic character, such as pyridine, quinoline, the various alkyl and dialkyl, preferably methyl and dimethyl derivatives thereof, imidazole, n-vinylimidazole, benzthiazole, 2-amino-6-ethoxy-benzthiazole, as well as phosphobenzenes.

E. Acid amides such as dimethyl formamide, diethyl formamide, N-dimethyl-acetamide, N-diethyl-propionamide, N-dimethyl benzamide, N-methyl-pyrrolidone, N,N'-tetramethyl-tere-phthalic acid amide, or ureas, for example tetramethyl urea and trimethylphenyl urea.

F. Other nitrogen or phosphorus compounds in which one nitrogen or phosphorus atom has a valence higher than 3, such as, for example, pyridine-N-oxide, trimethyl phosphine oxide, tributyl phosphine oxide, trihexyl phosphine oxide, triphenyl phosphine oxide, trimethyl phosphine sulfide, trihexyl phosphine sulfide, triphenyl phosphine sulfide, dimethylphenyl phosphine oxide, dimethyl-phenylphosphine sulfide, dimethylchloromethyl phosphine oxide, dimethyleicosyl phosphine oxide, dimethyldodecyl phosphine oxide, dimethyl phosphine oxide, dimethylpyrrolidine-1-methyl-phosphine oxide, triphenyl phosphine dichloride, dimethyldodecyl phosphine sulfide, triphenyl phosphine imine, dimethylchloromethyl phosphine dichloride, N-2-dimethylphosphinyl-ethylmethylacetamide, N-2-dimethylphosphinyl-ethylmethylamine, phospholene oxides, for example 1-methylphospholene-1-oxide and 1-ethyl-3-methylphospholene-1-oxide.

G. Amides of phosphinous and phosphonous acid, amides of phosphinic and phosphonic acid and the thio-analogs thereof, such as, for example, ethanephosphonic acid bis-diethyl amide, methane-butanephosphonous acid dimethyl amide, diethyl-phosphonous acid isobutyl amide, as well as triamides of phosphoric and thiophosphoric acid, for example hexamethyl phosphoric acid triamide.

The catalysts are used in an amount of from 0.01 to 5% by weight or more, calculated on the phosphonic acid derivative used, amounts in the range of from 0.5 to 2% by weight being preferred. They can be used as such or in the form of their salts, preferably the hydrochlorides. The catalysts are used either singly or in the form of mixtures or combinations. Usual inhibitors to prevent the vinyl-phosphonic acid halides from polymerizing may be added, for example hydroquinone or hydroquinone monomethyl ether.

The process of the invention is preferably carried out at a temperature in the range of from +65° to 200°°C. Higher temperatures are also possible, but in general they do not entail any advantage. Especially preferred temperatures are in the range of from +80° to +150° C.

The reaction may be carried out without pressure or under pressure, for example in the range of from 5 to 10 atmospheres gauge or, when the reaction is carried out without intermediate pressure release, even under higher pressures generated by the formation of $CO_2$ (CO).

The reaction time varies depending on the temperature and the apparatus used, in general it lasts for about 5 to 30 hours.

In general, an excess of acid halide beyond the stoichiometric amount is unnecessary, but it may serve to reduce the reaction time. The excess of acid halide, if any, which leaves the reaction zone together with the off-gases is then advantageously consumed by fresh starting product, expediently in a column in countercurrent flow. The entire process can likewise be carried out continuously in known manner in a column or an equivalent device.

To carry out the reaction the acid halide is preferably introduced into the mixture of phosphonic acid derivative and catalyst and the by-products, i.e. alkyl halide or alkali metal halide and $CO_2$ or CO, are removed in known manner, if possible already during the course of reaction, for example by distillation and/or fractional condensation.

In some cases it may be of advantage to add the catalyst in a later stage of the reaction, for example when it subsides.

Intense mixing of the reaction mixture is recommended, for example by vigorous stirring, even when gaseous acid halides are used, for example phosgene. When the reaction is terminated the reaction products are isolated by distillation.

Depending on the reaction conditions 2-chloroethane-phosphonic acid dichloride and vinyl-phosphonic acid dichloride are obtained side by side in different proportions, an increase in the reaction temperature, especially above 160° C, favoring the formation of vinylphosphonic acid dichloride. By fractional distillation of the reaction products without separation of the catalyst used the proportion of vinyl-phosphonic acid dichloride may also be augmented, especially at sump temperatures above 150° C.

The reaction products obtained by the process of the invention can be used in many fields of application. Vinylphosphonic acid dichloride, for example, is an important intermediate product for making vinyl phosphonic acid, plant protecting agents and flame retardants, 2-chloroethane-phosphonic acid dichloride is a valuable intermediate for the manufacture of maturity promotors and growth inhibitors.

The following examples illustrate the invention.

EXAMPLE 1

1 g of hydroquinone was added to 107 g (0.59 mole) of 2-hydroxyethane-phosphonic acid diethyl ester and the mixture was heated to 150° C. Next, phosgene was passed for 15 hours through the mixture while vigorously stirring, 1 g of pyridine was added and the passing through of phosgene was continued for a further 5 hours. 107 g of vinylphosphonic acid dichloride as solvent and another 1 g of pyridine as catalyst were added and phosgene was passed through for a further 3 hours at 150° C. In a water jet vacuum at room temperature the excess phosgene was removed from the reaction mixture and the remainder subjected to fractional distillation. 107 g of vinyl-phosphonic acid dichloride and 82 g of 2-chloroethane-phosphonic acid dichloride (boiling point 70° – 80° C under 3.5 mm Hg) still containing small amounts of vinyl-phosphonic acid dichloride were obtained. After deduction of the 107 g of vinyl-phosphonic acid dichloride used as solvent, the yield amounted to about 77% of the theory.

EXAMPLE 2

1 g of hydroquinone was added to 127.5 g (1.01 moles) of 2-hydroxyethane-phosphonic acid and the mixture heated to 130° C. 2 g of trimethyl phosphine sulfide were added as catalyst and phosgene was introduced for 4 hours while vigorously stirring.

The introduction of phosgene was continued for a further 10 hours at 170° – 180° C. Next, 1 g of pyridine was added and phosgene was passed through the mixture for a further 13 hours at 130° C. In a water jet vacuum the phosgene in excess was removed from the reaction mixture at room temperature and the residue was subjected to fractional distillation. 97 g of vinyl phosphonic acid dichloride, corresponding to a yield of 66% of the theory, and 20 g of 2-chloroethane-phosphonic acid dichloride, corresponding to a yield of 11% of the theory were obtained. The total yield thus amounted to 77% of the theory.

What is claimed is:

1. A process for the manufacture of halo-ethanephosphonic acid dihalides and vinyl-phosphonic acid dihalides of the formulae I and II

in which X represents halogen, which comprises reacting hydroxy-ethane-phosphonic acid of the formula

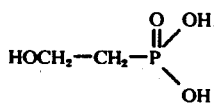
(III)

a salt or an ester thereof with an acid halide of the formula $(CO)_nX_2$     (IV)

in which X has the meaning defined above and n stands for 1 or 2, in the presence of a catalyst consisting of a compound that:

contains at least one nitrogen or phosphorous atom which is bound by three or four valences to carbon, two valences possibly forming a double bond and further has the formula V, VI, or VII:

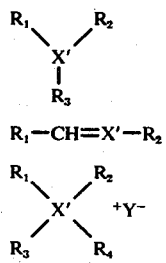

(V), (VI), (VII), in which X' represents a nitrogen or phosphorous atom, Y is an inorganic or organic acid radical, and $R_1$, $R_2$, $R_3$, and $R_4$ are identical or different organic radicals which are straight chain or branched alkyl radicals having from 1 to 20 carbon atoms, alkenyl radicals having from 2 to 20 carbon atoms, cycloalkyl radicals having from 4 to 8 carbon atoms, or phenyl or benzyl groups or acyl groups having from 1 to 4 carbon atoms, all radicals $R_1$ to $R_4$ possibly being substituted by halogen, or alkoxy having from 1 to 4 carbon atoms, or a dialkyl-amino group the alkyl groups of which have from 1 to 4 carbon atoms, two of the radicals $R_1$ to $R_4$ may form a ring, and the catalyst has a molecular weight of up to 500; or contains a nitrogen or phosphorus atom bound by three valences to carbon and has the formula VIII:

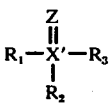

(VIII)

in which Z represents oxygen or, if X' is phosphorus, Z also represents sulfur, two halogen atoms, or the group $NR_5$ in which $R_5$ has the same meaning as $R_1$ or represents hydrogen, and 2 or 3 of the radicals $R_1$ to $R_3$ may form a cycle, optionally including for example oxygen, sulfur, or nitrogen as a heteroatom.

2. A process as claimed in claim 1, wherein the reaction is carried out in the presence of an inert solvent.

3. A process as claimed in claim 1, wherein X in formulae I, II and IV is chlorine or bromine.

4. A process as claimed in claim 1, wherein phosgene is used as acid halide of formula IV.

5. A process as claimed in claim 1, wherein the compound of formula III is used in the form of the free acid, an alkali metal or ammonium salt or a neutral alkyl ester having from 1 to 6 carbon atoms in the alkyl radical.

6. A process as claimed in claim 1, wherein the catalyst is used in an amount of from 0.01 to 5% by weight, calculated on the phosphonic acid component.

7. A process as claimed in claim 1, wherein triethyl amine, pyridine or trimethyl-phosphine sulfide is used as catalyst.

8. A process as claimed in claim 2, wherein the final product of the reaction is used as inert solvent.

9. A process as claimed in claim 2, wherein hydroquinone or hydroquinone monomethyl ether is used as a polymerization inhibitor.

10. A process as claimed in claim 1, wherein the reaction is carried out at a temperature of from 65° to 200° C.

11. A process as claimed in claim 10, wherein the reaction is carried out at a temperature of from 80° to 150° C.

12. A process as claimed in claim 1, wherein Y is a halogen ion, a sulfate ion, or an organic sulfonate; $R_1$ to $R_4$ are alkyl radicals having from 1 to 4 carbon atoms, alkenyl radicals having from 2 to 4 carbon atoms, or cycloalkyl radicals having from 4 to 6 carbon atoms.

13. A process for the manufacture of halo-ethane-phosphonic acid dihalides and vinyl-phosphonic acid dihalides of the formulae I and II

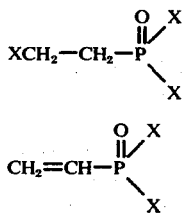

(I)

(II)

in which X represents halogen, which comprises reacting with intense mixing hydroxy-ethane-phosphonic acid of the formula

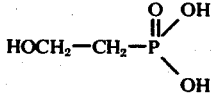

(III)

a salt or an ester thereof, with an acid halide of the formula $(CO)_nX_2$     (IV)

in which X has the meaning defined above and n stands for 1 or 2, in the presence of a catalyst chosen from the group consisting of:

trimethylamine, tripropylamine, tributylamine, triphenylamine, trimethyl phosphine, triethyl phosphine, tripropyl phosphine, tributyl phosphine, triphenyl phosphine, and tris (p-dimethylaminophenyl)-phosphine, dimethylamine, diethylbutylamine, N-dimethyl-aniline, 4-methyl-N-dimethylaniline, diethylaniline, N,N-tetramethylphenylene diamine, and N-methylpyrrolidone; methyldiethyl phosphine, dimethylpropyl phosphine, diethylbenzyl phosphine, 1-methylphospholene-3, 1-ethyl-3- methylphospholene-3; hydrobenzamide, benzalaniline, O-, m-, p-methyl-, o-, m-, p-methoxy-, o-, m-, 10-chloro-benzalaniline, - the corresponding derivatives of the substituted anilines, O-, m-, p-toluidine, o-, m-, p-nitraniline, o- and p-anisidine and o-, m-, and p-chloroaniline; tetramethylammonium chloride or bromide, tetraethyl-phosphonium chloride, trimethylbenzylammonium chloride, triethylbenzylammonium chloride, trimethylbenzyl-phosphonium chloride, triphenylethyl-phosphonium-2,4-diaminobenzene sulfonate; pyridine, quinoline, the methyl and dimethyl derivatives of the latter two, imidazole, n-vinylimidazole, benzthiazole, 2-amino-6-ethoxybenzthiazole, phosphobenzenes; dimethyl formamide, diethyl formamide, N-dimethyl-acetamide, N-diethyl-propionamide, N-dimethyl-benzamide, N-methyl-pyrrolidone, N,N'-tetramethyl-terephthalic acid amide, tetramethyl urea, trimethylphenyl urea; pyridine-N-oxide, trimethyl phosphine oxide, tributyl phosphine oxide, trihexyl phosphine oxide, triphenyl phosphine oxide, trihexyl phosphine sulfide, triphenyl phosphine sulfide, dimethylphenyl phosphine oxide, dimethyl-phenylphosphine sulfide, dimethylchloromethyl phosphine oxide, dimethyleicosyl phosphine oxide, dimethyldodecyl phosphine oxide, dimethyl phosphine oxide, dimethyl pyrrolidine-1-methyl-phosphine oxide, triphenyl phosphine dichloride, dimethyldodecyl phosphine sulfide, triphenyl phosphine imine, dimethylchloromethyl phosphine dichloride, N-2-dimethylphosphinyl-ethylmethylacetamide, N-2-dimethylphosphinyl-ethylmethylamine, 1-methylphospholene-1-oxide, 1-ethyl-3-methylphospholene-1-oxide; ethane-phosphinic acid bis-diethyl amide, methane-butane-phosphonous acid dimethyl amide, diethyl-phosphonous acid isobutyl amide, hexamethyl phosphoric acid triamide; and mixtures thereof.

14. A process as claimed in claim 1, wherein X in formulae I, II, and IV is chlorine or bromine; the acid halide of formula IV is selected from the group consisting of oxalyl chloride, bromophosgene, oxalyl bromide and phosgene, the compound of formula III is used in the form of the free acid, an alkali metal or ammonium salt, or a neutral alkyl ester having from 1 to 6 carbon atoms in the alkyl radical; the catalyst is used in an amount from 0.01 to 5% by weight, calculated on the phosphonic acid component; triethyl amine, pyridine or trimethyl-phosphine sulfide is used as the catalyst; and the inert solvent is equivalent to the final products of the reaction.

15. A process as claimed in claim 14, wherein hydroquinone or hydroquinone monomethyl ether is used as a polymerization inhibitor; the reaction is carried out at a temperature of from 65° to 200° C and under a pressure of from about 5 to about 10 atmospheres and for a time of from about 5 to about 30 hours.

16. A process as claimed in claim 5, wherein the compound of Formula III is in the form of the free acid.

17. A process as claimed in claim 5, wherein the compound of Formula III is in the form of a neutral alkyl ester having from 1 to 6 carbon atoms in the alkyl radical.

18. A process as claimed in claim 5, wherein the compound of Formula III is in the form of an alkali metal or ammonium salt.

19. A process as claimed in claim 16, wherein X in Formulae I and II is chlorine; the acid halide of Formula IV is phosgene.

20. A process as claimed in claim 17, wherein X in Formulae I and II is chlorine; the acid halide of Formula IV is phosgene.

21. A process as claimed in claim 18, wherein X in Formulae I and II is chlorine; the acid halide of Formula IV is phosgene.

22. The process as claimed in claim 19 wherein a polymerization inhibitor is used.

23. The process as claimed in claim 20 wherein a polymerization inhibitor is used.

24. The process as claimed in claim 21 wherein a polymerization inhibitor is used.

* * * * *